United States Patent [19]

Stade

[11] 4,096,637
[45] Jun. 27, 1978

[54] ORIENTING DEVICE FOR DENTAL FACEBOW OR PANTOGRAPH

[76] Inventor: Elwood H. Stade, R.R. #3 Box 369C, Edwardsville, Ill. 62025

[21] Appl. No.: 679,465

[22] Filed: Apr. 22, 1976

[51] Int. Cl.² .................. A61C 19/04; G01C 9/28
[52] U.S. Cl. .................... 33/174 D; 32/20; 33/334; 33/383
[58] Field of Search .......... 33/174 D, 180 R, 333, 33/334, 354, 383, 384, 385, 386, 387, 388; 32/14 D, 20

[56] References Cited

U.S. PATENT DOCUMENTS

| 312,266 | 2/1885 | Gurley | 33/373 |
|---|---|---|---|
| 1,070,123 | 8/1913 | Evans | 33/373 |
| 1,753,965 | 4/1930 | Ralph | 33/174 D |
| 1,786,915 | 12/1930 | McLean | 33/174 D |
| 1,815,949 | 7/1931 | Marischal | 33/383 |
| 2,412,495 | 12/1946 | Daly et al. | 33/384 |
| 3,693,260 | 9/1972 | Hernandez | 32/20 |

*Primary Examiner*—Richard E. Aegerter
*Assistant Examiner*—Richard R. Stearns

[57] ABSTRACT

An orienting device for a dental facebow which consists of a first gauge and a second gauge which are arranged for pivotal movement with respect to the facebow in planes which are perpendicular to one another. The gauges are of the bubble gauge type, and by pivotal movement each can be arranged in a horizontal attitude, so that the normal attitude of the upper jaw of a patient may be measured and reproduced exteriorly of the mouth of the patient.

3 Claims, 6 Drawing Figures

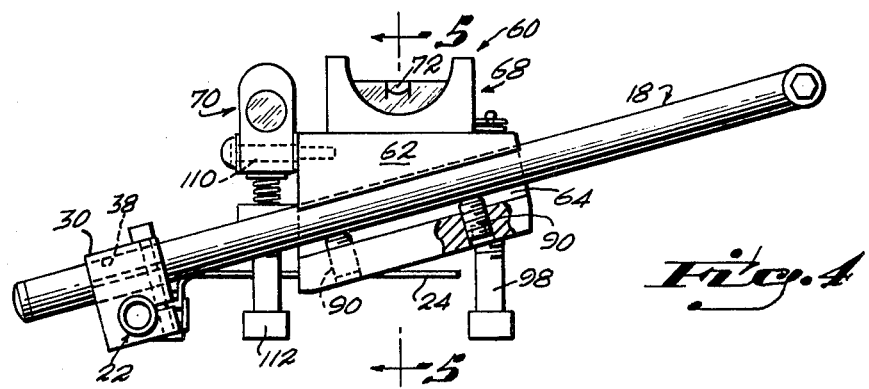
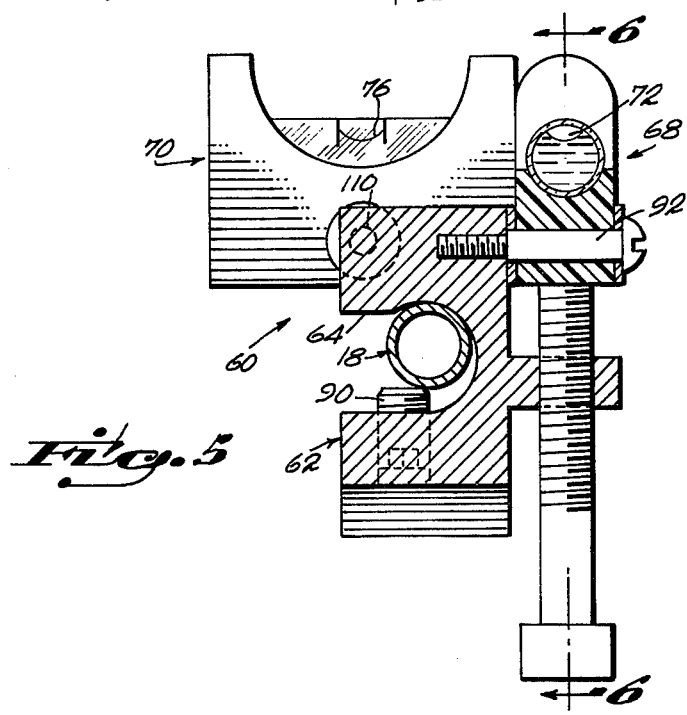
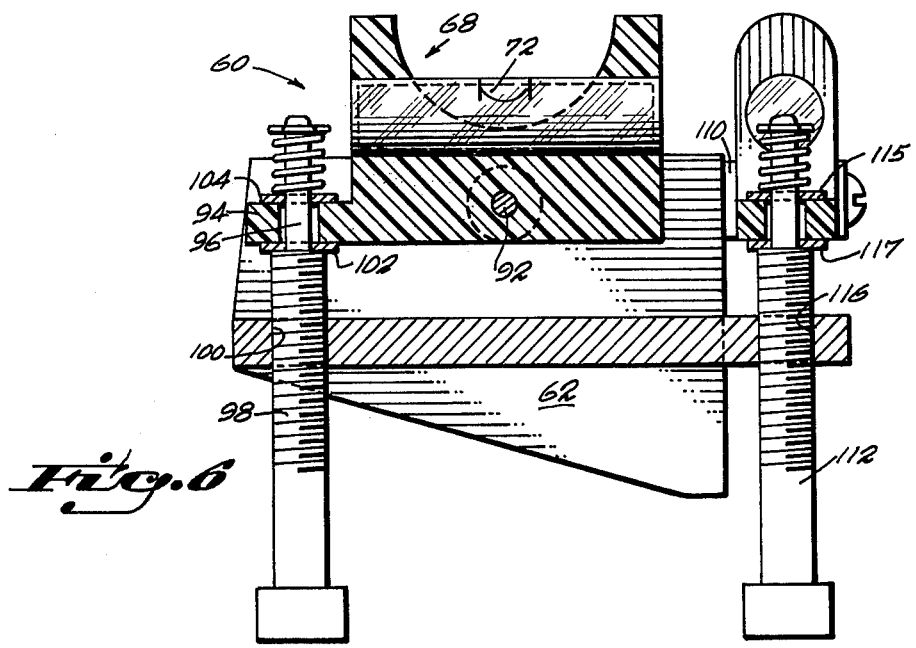

ORIENTING DEVICE FOR DENTAL FACEBOW OR PANTOGRAPH

Field of the Invention

This invention relates to dental devices and more particularly to a device to orient a dental facebow or pantograph.

Background of the Invention

When a dentist wishes to do bridgework or denture work, etc., an impression of the teeth or jaws of the patient is made by inserting a material in the mouth and, later, fabricating a plaster cast from it so that the dental appliance can be fabricated extraorally. In addition to merely making a cast of the teeth, it is good practice to record the working interrelationship of the teeth in the mouth because the lower jaw teeth must cooperate with the upper jaw teeth. In order to do this, the relationship of the maxilla or upper jaw of the particular patient in relation to space should be recorded as a reference. In the past there have been numerous attempts to provide a device. In other words, in order that dental casts be complete one should take into consideration the position in space as well as the working interrelationship of the teeth. This can be done by measuring the position of the maxilla of the patient as a reference which once recorded can then be transferred to a stand called an articulator, on which the dental casts are mounted for fabricating the materials to be inserted in the mouth.

In the past, devices to do this, known as facebows, have been used; however, no accurate means of recording the relationship of the maxillary jaw to the three dimensions of space have been provided. Such is necessary in order to accomplish an accurate portrayal of the maxilla. Most of the facebows of the prior art merely measure the anterior/posterior distance of the maxilla to the hinge axis of the jaws. It is conventional in the prior art to locate the hinge axis of the lower jaw of a patient and to mark that on the skin of the left and right side of his head. This axis can be found without difficulty by an emperically determined measurement or by mechanical means. Once the hinge axis of the jaws is found, the following steps take place:

The patient first bites on a wax-type material to make an impression in it. The wax impression is removed from the mouth, and it is attached to the facebow being used. The impression, attached to the facebow, is then inserted back into the patient's mouth and a measurement is made of the distance of the impression from the hinge axis. Without referring in detail to FIG. 3, it will suffice at this point to state that the impression, there shown mounted, is positioned in the patient's mouth as shown in FIG. 2, and, thereafter, the left and right-hand side rods of the facebow are extended longitudinally in one direction or the other until the points at the bottom of FIG. 3, which confront one another, are located at the hinge axis of the jaw of the patient. This is done, as shown in FIG. 2, by positioning those points as shown.

Thus, the prior art teaches the use of facebows as a tool to measure the distance of the patient's maxillary jaw from the hinge axis.

This invention is of a device which can be attached to a conventional facebow which makes it possible to measure in addition the angle of inclination of the plane of the upper jaw, namely, the superior/inferior inclination of the maxilla of the patient; and, additionally, to measure the sagittal inclination of the maxilla of the patient, so that the impression can be transferred to an articulator, which is simply a device on which the impression is mounted to do work outside the mouth.

Generally speaking, therefore, it is an object of this invention to provide means to measure and record the relationship of the maxillary jaw of a patient to reproduce its proper attitude and relationship in space so that work can be done using the impression outside of the mouth.

While the foregoing sets forth the background generally of this invention, it will be helpful to consider the following.

The instrument of the present invention is for use in conjunction with either a dental facebow or pantograph and provides structure whereby the relationship of the maxillary jaw to the three dimensions of space may be recorded and reproduced on an articulator for use in doing the necessary work outside of the mouth using the impression. The invention permits the relationship to be accurately transferred to a dental articulator where a plaster cast of the maxillary jaw can be mounted in the exact same position with respect to space that it normally occupies in the patient's mouth.

Objects of the Invention

This invention has the following objects: At the present time there is no accurate means to record and orient a facebow or pantograph to the sagittal plane of a patient. This is an essential record since facial asymetries exist and the location of axis points which dictate this position may not be symmetrically located on the face. If asymetrical axis points are recorded and then transferred to a dental articulator, whose receiving axis points are parallel to the horizontal plane, the maxillary dental cast will be mounted in a canted position. The dental technician has no means of assessing the faulty cast placement and so fabricates his anterior tooth replacements in reference to the horizontal plane which incorporates error. This invention has as an object the removal of this source of error by the use of the anterior level gauge designated by the numeral 70 in FIGS. 3 and 4. This gauge will record any cant of the facebow or pantograph so it may be duplicated when mounting it to an articulator by adjusting the articulator until the bubble of the gauge is centered.

The superior-inferior position, or second dimension, must also be determined when mounting the maxillary cast to an articulator. The cast, as mentioned previously, has been related to the hinge axis position of the lower jaw by means of the facebow or pantograph. This cast may be rotated, by means of the appartus, around the hinge axis of the articulator to alter the superior-inferior positioning of the cast. Some instruments have mechanical marks to determine the positioning of the cast but this only facilitates locating the cast midway between the upper and lower member of the articulator. Some facebows and pantographs have a pointer that contacts the anterior reference point and it is, likewise, used to orientate the cast to the horizontal plane. Studies have shown this technique to be in error. The present invention records and transfers the exact position of the transfer apparatus when the patient's head was in the normal erect postural position. This is done by setting the level gauge 68 see FIGS. 3 and 4 by means of an adjustment screw. This position of the cast is important for anterior tooth esthetics. If the maxillary cast is mounted too low, the anterior teeth will flare when returned to the mouth. If the maxillary cast is mounted too high, the maxillary teeth will be retruded in the patient's mouth. By having recorded the exact position of the transfer instrument on the face of the patient with the level gauge, a user is capable of reproducing this position on the articulator by merely raising or lowering the facebow or pantograph with respect to the articulator until the level gauges show that they are in the exact horizontal setting which simulates the patient's maxilla in space. This is another object which may be accomplished by this invention.

The third dimension in space is the anterior-posterior positioning of the maxillary cast on the articulator. This has been dictated by the accurate positioning of the facebow or pantograph to the hinge axis points, a step which is known in the prior art.

Thus, by using this invention the maxillary dental cast can be accurately oriented on the dental articulator in three dimensions in space with a minimal amount of time and, accordingly, this is an important object of this invention.

It is a further object of this invention to provide an orientator for a dental facebow or pantograph which is small and light in weight and which includes adjustment means for gauges for ease of use and which in general will provide for improved performance and increased accuracy in prosthodontic dentistry.

In accordance with these and other objects which will become apparent hereinafter, the instant invention will now be described with reference to the accompanying drawings in which:

Description of the Drawings:

FIG. 4 is a view of the facebow in space as shown applied to a patient's head;

FIG. 5 is a view in cross section taken on the plane indicated by the line 5—5 of FIG. 4 and looking in the direction of the arrows;

FIG. 6 is a view in cross section taken on the plane indicated by the line 6—6 of FIG. 5 and looking in the direction of the arrows.

Figure 1:
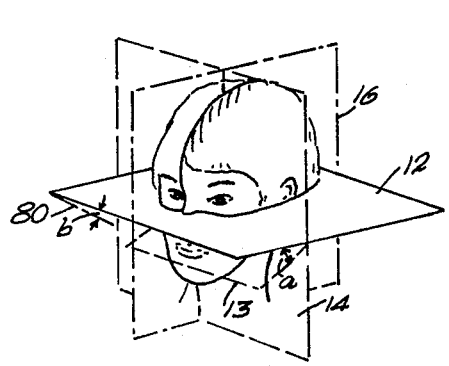
FIG. 1 is a perspective view to illustrate a patient's head in various reference planes.

Description of Preferred Embodiment:

Referring to the drawings wherein like reference characters designate like or corresponding parts throughout the several views, the numeral 12 in FIG. 1 designates a horizontal plane through the hinge axis of a patient's jaw. The plane generally designated by the numeral 14 is inclined with respect to the horizontal plane 12 at an angle a, see FIG. 2 for the reference to the angle. Referring back to FIG. 1, the numerals 14 and 16 are the other vertical planes which are perpendicular to the horizontal plane and which are perpendicular with respect to one another comprising three planes in space.

Figure 3:
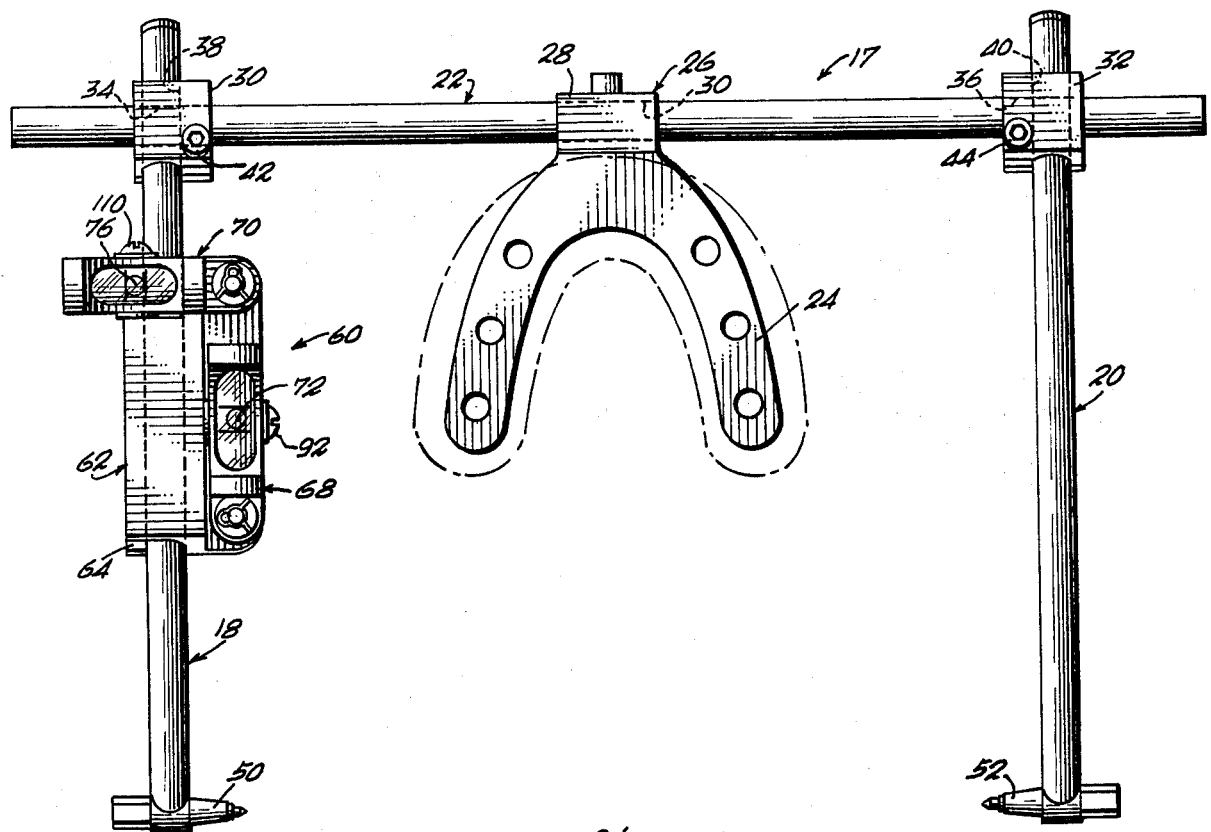
FIG. 3 is a top view of the facebow shown in FIG. 1.

Referring to FIG. 3 the numeral 17 generally designates a facebow with side portions 18 and 20 and a forward portion 22. As shown, the forward portion 22 includes a holder 24 for impression medium, usually wax, and means 26 to mount it to the forward portion of the facebow. The means to mount it includes a slide block 28 from which the holder extends; and this slide block includes a lateral hole 30 through it which permits shifting adjustment by sliding it to the left or right.

Conventionally, a screw, not shown, is used which extends through the slide block and into engagement with the forward portion to fix it and the holder in a predetermined position on the forward portion of the facebow. The side portions 18 and 20 of the facebow each are connected to the forward portion 22 of the facebow by slide blocks 30 and 32 each with a hole 34 and 36 therethrough to accommodate shifting movement of the side portions. Also the slide blocks include holes 38 and 40 for longitudinal adjustment or movement of the side portions with respect to the forward portion of the facebow. The screw means generally designated by the numerals 42 and 44 are utilized to tighten the facebow together in a fixed position depending upon the width of the person's face and the distance from the hinge joint of the jaw of the patient to the holder on which the wax is located when an impression is to be made. It will be seen that on the extending terminal ends of the portions 18 and 20 locater pins 50 and 52 are provided.

In use, wax is positioned in the holder, the holder is positioned in the patient's mouth. The pins 50 and 52 are located so as to define a line coincident with the hinge axis of the jaw while the patient bites on the wax in the holder. Thus, an impression is made.

Reference will now be made to the portion of FIGS. 4–6. The orienting means is generally designated by the numeral 60. It includes a housing on one of the side portions of the facebow, which is generally designated by the numeral 62; and it also includes a longitudinally extending recess 64 sized for mating engagement and connection with the side bow, as shown. It also includes, on the housing, a first leveling gauge 68 and a second leveling gauge 70.

Figure 2:
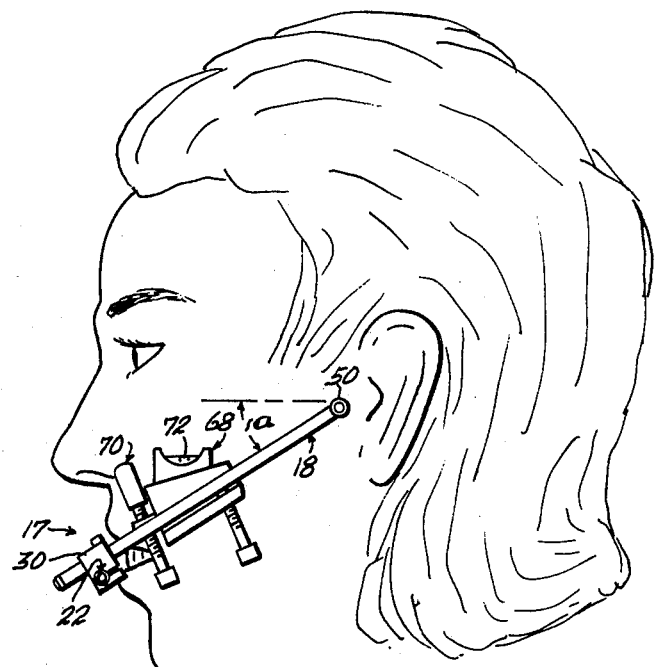
FIG. 2 is a side elevation view of a patient to which a facebow which includes the instant invention has been applied.

In use, once the facebow is placed on a patient's face as shown, and while he is biting on the impression, the dentist orients the patient's head in a correct attitude, see in FIG. 2, that is with his eyes looking forward in a horizontal plane. The leveling device 68 is tilted with respect to the facebow side portion 18 until the bubble 72 of the gauge 68 is in the middle of the gauge marks, see FIG. 3. The second gauge 70 is also tilted until the bubble 76 is in the middle of the gauge 70. Thus, the angle of inclination a is recorded and, additionally, the angle of inclination b of the plane 80 with respect to the plane 12, see FIG. 1, is also recorded. Thereafter, the facebow is removed from the patient and positioned on an articulator with the points 50 and 52 being received in a proper location and the articulator is adjusted until the bubbles are as shown in FIG. 3. When this has been done, it simulates the position in space of the maxillary or upper jaw of the patient.

Reference will now be made to FIGS. 4, 5 and 6, which are chiefly of the orienting device for attachment to the facebow side portion. On reference to FIGS. 4 and 5, it is seen that the housing 62 includes the screw means 90 for connection to the side portions 18 of the facebow. The gauge 68 is pivotally mounted to the housing on a pivot pin as at 92 and includes a portion 94 extending outwardly therefrom which is engaged by an extending portion 96 of a screw 98 which threadably engages a hole 100 in the housing, whereby when the screw is turned, the screw, through the plate 102 will bear against the portion 94 moving it upwardly in a pivotal direction or, when the screw is retracted will move it in the opposite direction of rotation as the plate 104 bears against the other side of the extension 94. Thus, the gauge 68 may be tilted until the bubble is in the center. Similarly, the gauge 70 is pivotally mounted to the housing as at 110 and includes an adjustment screw 112 which is in threaded engagement through a hole 116 of the housing to tilt the gauge 70 about the axis as the screw pushes or pulls on the plates 115 or 117.

Thus, once the facebow is applied to a patient, and while he bites on it, and while his head is oriented in a proper direction, the dentist adjusts the screws which levels the bubbles and by so doing records the orientation in space of the patient's maxilla with respect to the angles *a* and *b* shown in FIG. 1.

What is claimed is:

1. In combination, a facebow and facebow orienting means, said facebow comprising a first and a second spaced temple portion and a transverse portion, said facebow being adapted to encircle the frontal face zone of a patient, said orienting device comprising a body, a first leveling gauge means including first pivotal means pivotally connecting said first leveling gauge means to the body for swinging movement in a first vertical plane, a second leveling gauge means including second pivotal means pivotally connecting the second leveling gauge means to the body for pivotal movement of said second leveling gauge means in a vertical plane perpendicular to the plane of pivotal movement of said first leveling gauge means, and adjustment means to pivotally move the gauges with respect to the body and to hold the gauges to the body in adjusted positions, and means to mount the body to said facebow with said first leveling gauge means being oriented generally parallel to a line connecting the ends of said temple portions, and said second leveling gauge means lying in a generally horizontal plane when said facebow is in its use position.

2. The device as set forth in claim 1 wherein said adjustment means comprises a pair of threaded screws and said body includes a first hole and a second hole, each of said threaded screws having a terminal end and each being in threaded engagement in one of said holes, the terminal end of one of said screws being in engagement with said first gauge means and means connecting the terminal end of said one of said screws to the first gauge means and the terminal end of the other of said screws being in engagement with said second gauge means and means connecting the terminal end of said other of said screws to said second gauge means.

3. A facebow, orienting device, and means to mount the orienting device to said facebow, said facebow comprising first and second generally parallel spaced temple portions and said device comprising a body including first and second bubble gauges, each bubble gauge having a longitudinal axis arranged in perpendicular relation with respect to one another and each including means for mounting the bubble gauges to the body for pivotal movement in planes perpendicular to one another, and adjustments means for pivotally moving the bubble gauges with respect to the body, and holding means for holding the bubble gauges in selected positions, and said means mounting said device comprising means for attaching said orienting device to one of said temple portions with the longitudinal axis of said first bubble gauge being oriented generally parallel to a line connecting the temple portions and perpendicular to said temple portions and the said second gauge lying in a generally horizontal plane when said facebow is in its use position.

* * * * *